(12) United States Patent
Weiss et al.

(10) Patent No.: US 8,309,511 B1
(45) Date of Patent: Nov. 13, 2012

(54) 3(OR 2),4,5-TRIMETHYL-OCTAHYDRO-4,7-METHANO-INDEN-5-OL AND ITS USE IN PERFUME COMPOSITIONS

(75) Inventors: Richard A. Weiss, Livingston, NJ (US); Anubhav P. S. Narula, Hazlet, NJ (US); James Anthony Lasome, Matawan, NJ (US); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/477,114

(22) Filed: May 22, 2012

(51) Int. Cl.
*A61K 7/46* (2006.01)
*C07C 35/22* (2006.01)

(52) U.S. Cl. ............. 512/19; 512/14; 568/819; 568/820

(58) Field of Classification Search .................... 512/14, 512/19; 568/819, 820
See application file for complete search history.

(56) References Cited

OTHER PUBLICATIONS

Chemical abstract, Nazarov et al, Acetylene derivatives. CXCV. transformation of cyclopentenones, Zhurnal Obshchei Khimi (1960), 30, 450-462.*

* cited by examiner

*Primary Examiner* — Jafar Parsa
(74) *Attorney, Agent, or Firm* — Elizabeth M. Quirk; Xu Fan Tseng; Joseph F. Leightner

(57) ABSTRACT

The present invention is directed to novel fragrance compounds and their unexpected advantageous use in enhancing, improving or modifying a fragrance formulation through the addition of an olfactory acceptable amount of the compounds, wherein the compounds are represented by the following formula:

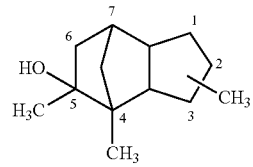

wherein a methyl group is bonded to the 5-membered ring at position 2 or 3, or a mixture thereof.

20 Claims, No Drawings

3(OR 2),4,5-TRIMETHYL-OCTAHYDRO-4,7-METHANO-INDEN-5-OL AND ITS USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

SUMMARY OF THE INVENTION

The present invention provides novel chemicals and their unexpected advantageous use in enhancing, improving or modifying the fragrance of perfumes, colognes, toilet waters, personal products, fabric care products, and the like.

Specifically, the present invention relates to a novel 4,7-methano-indenol represented by Formula I set forth below:

Formula I

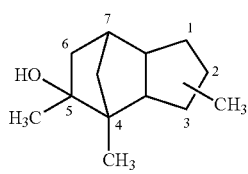

wherein a methyl group is bonded to the 5-membered ring at position 2 or 3, or a mixture thereof.

More specifically, the present invention relates to novel 4,7-methano-indenols represented by Formula II and Formula III set forth below:

Formula II

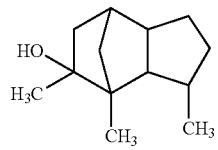

Formula III

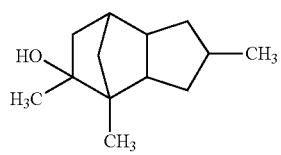

and a mixture thereof.

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

Those with skill in the art will recognize that Formula II provided above represents 3,4,5-trimethyl-octahydro-4,7-methano-inden-5-ol; and Formula III provided above represents 2,4,5-trimethyl-octahydro-4,7-methano-inden-5-ol. It has been surprisingly found that the compounds of the present invention provide unexpected strong patchouli characteristics.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention were prepared with hexahydro-3(or 2),4-dimethyl-4,7-methano-inden-5-ol (commercially available at International Flavors &Fragrance, Inc.) according to the following reaction schemes, the details of which are specified in the Examples. Additional materials and catalysts were purchased from Aldrich Chemical Company.

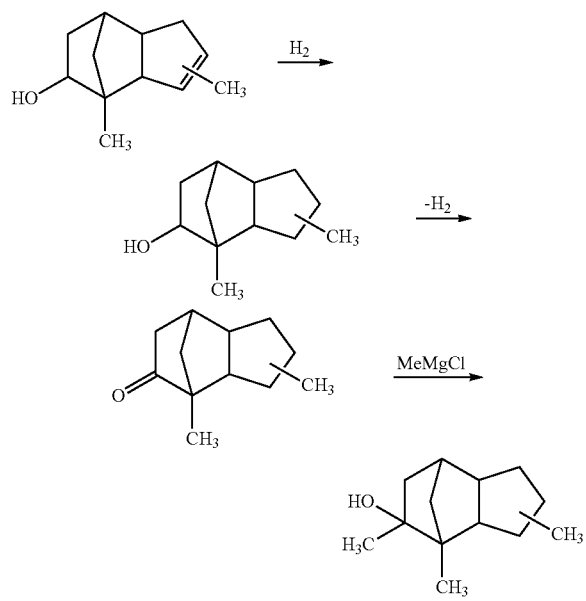

wherein the methyl group is bonded to the 5-membered ring at position 2 or 3 as indicated in the above; and wherein H₂ represents hydrogenation, —H₂ represents dehydrogenation, and MeMgCl represents methyl magnesium chloride.

In additional, mixtures containing specific ratios of 3,4,5-trimethyl-octahydro-4,7-methano-inden-5-ol (Formula II) and 2,4,5-trimethyl-octahydro-4,7-methano-inden-5-ol (Formula III) were obtained. It has been found that mixtures containing no less than 50% by weight of 3,4,5-trimethyl-octahydro-4,7-methano-inden-5-ol possesses desirable fragrance properties of high strength.

Those with skill in the art will recognize that the product mixture obtained as described above can be separated using techniques known to those with skill in the art. Suitable techniques include, for example, distillation and chromatography such as high performance liquid chromatography, referred to as HPLC, particularly silica gel chromatograph, and gas chromatography trapping known as GC trapping. Yet, commercial products are mostly offered as isomeric mixtures.

Those with skill in the art will further recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art as described above.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexylon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo [7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl- 5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides fruity, sweet, and green notes to make the fragrance formulation more desirable and noticeable, and add the perception of value. The odor qualities found in this material assist in beautifying and enhancing the finished accord as well as improving the performance of the other materials in the fragrance. There is also the fruity side of it which is found in many fragrances today which happens to be very trendy in vogue, especially for the younger consumers.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, M is understood to be moles per liter, mmHg be millimeters (mm) of mercury (Hg), and psig is understood to be pound-force per square inch gauge. IFF as used in the examples is understood to mean International Flavors & Fragrances Inc., New York, N.Y., USA.

EXAMPLE I

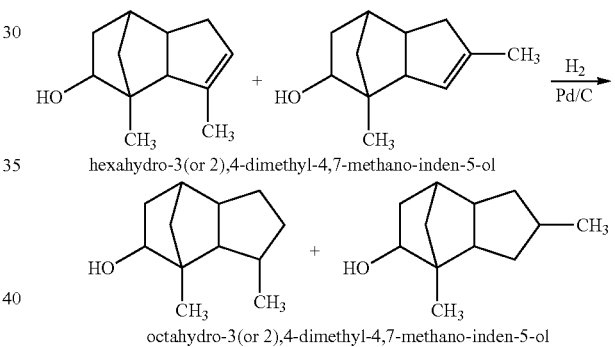

hexahydro-3(or 2),4-dimethyl-4,7-methano-inden-5-ol octahydro-3(or 2),4-dimethyl-4,7-methano-inden-5-ol Preparation of Octahydro-3(or 2),4-dimethyl-4,7-methano-inden-5-ol: A 2-L ZipperClave® was charged with hexahydro-3(or 2),4-dimethyl-4,7-methano-inden-5-ol (a mixture of hexahydro-3,4-dimethyl-4,7-methano-inden-5-ol and hexahydro-2,4-dimethyl-4,7-methano-inden-5-ol in a ratio of 60:40) (1.6 Kg, 9.04 mol, commercially available at IFF) and palladium carbon catalyst (Pd/C) (16 g, commercially available at Evonik Degussa Corporation). The ZipperClave® was flushed and vented three times with nitrogen ($N_2$), followed by three times with hydrogen ($H_2$). The ZipperClave® was then subsequently pressurized to 100 psig with $H_2$ and heated to 80° C. Gas-liquid chromotography (GLC) indicated the completion of the reaction after about 3 hours. The reaction mixture was then purged and vented three times with $N_2$ to provide the crude product, which was distilled to afford octahydro-3(or 2),4-dimethyl-4,7-methano-inden-5-ol (a mixture of octahydro-3,4-dimethyl-4,7-methano-inden-5-ol and octahydro-2,4-dimethyl-4,7-methano-inden-5-ol in a ratio of 60:40) with a boiling point of 122° C. at a pressure of 15 mmHg (1.553 Kg).

$^1$H NMR (CDCl$_3$, 400 MHz): 0.54-2.3 ppm (m, 13H), 0.97 ppm (d, ~60% of 3H, J=6.0 Hz), 1.01 ppm (d, ~40% of 3H, J=6.0 Hz), 1.02 ppm (s, ~60% of 3H), 1.09 ppm (s, ~40% of 3H), 3.30-3.35 ppm (m, 1H)

Octahydro-3(or 2),4-dimethyl-4,7-methano-inden-5-ol obtained as above was described as having weak woody, weak patchouli, and camphoraceous notes.

EXAMPLE II

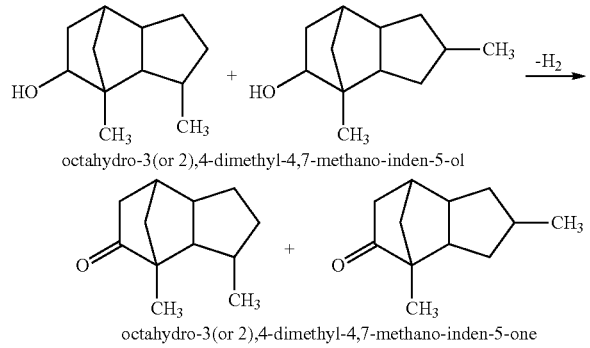
octahydro-3(or 2),4-dimethyl-4,7-methano-inden-5-ol
octahydro-3(or 2),4-dimethyl-4,7-methano-inden-5-one Preparation of Octahydro-3(or 2),4-dimethyl-4,7-methano-inden-5-one: A 5-L 3-neck reaction flask equipped with a mechanical stirrer, an addition funnel, a Dean-Stark trap, a condenser, a nitrogen ($N_2$) bubbler, and a thermocouple was charged with octahydro-3(or 2),4-dimethyl-4,7-methano-inden-5-ol (150 g, 0.83 mol, prepared as above in Example I), Primol (50 g), and PriCat CZ 30/18 P (commercially available from Johnson Matthey Corporation, U.S.) (64 g). The reaction temperature was heated to 240° C. Hydrogen gas ($H_2$) evolution was monitored via the N2 bubbler. Once the $H_2$ was observed, additional octahydro-3(or 2),4-dimethyl-4,7-methano-inden-5-ol (1.4 Kg, 7.78 mol) was fed in the reaction flask over 4 hours. After the feeding was complete, the reaction was further aged for 2 hours. Gas-liquid chromatography (GLC) indicated a conversion rate of ~95%. The crude product was filtered and distilled to afford octahydro-3(or 2),4-dimethyl-4,7-methano-inden-5-one (a mixture of octahydro-3,4-dimethyl-4,7-methano-inden-5-one and octahydro-2,4-dimethyl-4,7-methano-inden-5-one in a ratio of 60:40) with a boiling point of 135° C. at a pressure of 2 mmHg (1.368 Kg).

$^1$H NMR (CDCl$_3$, 400 MHz): 2.20-2.26 ppm (m, 2H), 2.11 ppm (d, ~42% of 1H, J=4.60 Hz), 2.07 ppm (d, ~58% of 1H, J=4.56 Hz), 1.76-1.95 ppm (m, 4H), 1.63-1.72 (m, 1H), 1.26-1.35 ppm (m, 2H), 1.11 ppm (s, 3H), 1.06-1.18 ppm (m, 2H), 1.03 ppm (d, 3H, J=6.44 Hz).

Octahydro-3(or 2),4-dimethyl-4,7-methano-inden-5-one obtained as above was described as having weak woody, weak earthy, and camphoraceous notes.

EXAMPLE III

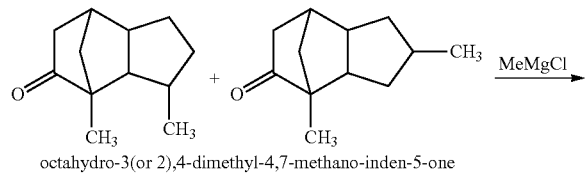
octahydro-3(or 2),4-dimethyl-4,7-methano-inden-5-one

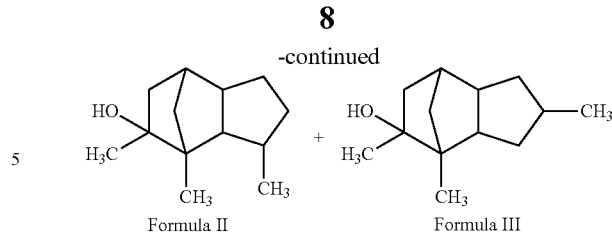
Formula II
Formula III

Preparation of 3(or 2),4,5-Trimethyl-octahydro-4,7-methano-inden-5-ol (Formula II and Formula III): A flame-dried, 5-L 3-neck reaction flask equipped with a mechanical stirrer, an addition funnel, a condenser, and a thermocouple was charged with MeMgCl in tetrahydrofuran (THF) (3 M, 1.6 L) under $N_2$. The temperature was cooled to and maintained at 15-20° C. using an external isopropyl alcohol (IPA) cooling bath. Octahydro-3(or 2),4-dimethyl-4,7-methano-inden-5-one (744 g, 4.1 mol, prepared as above in Example II) was fed in the reaction flask over 3-4 hours. The reaction temperature was allowed to rise to and maintained at 30° C. for 1 hour. The reaction mixture was subsequently quenched with acetic acid (HOAc) (279 g, 4.5 mol) and ice. The organic layer was washed once with dilute sodium carbonate solution (500 mL, 2%) and separated to afford the crude product, which was further distilled to afford 3(or 2),4,5-trimethyl-octahydro-4,7-methano-inden-5-ol (a mixture of Formula II and Formula III in a ratio of 60:40) with a boiling point of 108° C. at a pressure of 1 mmHg (732 g). Distillation was further employed to separate individual components.

3,4,5-Trimethyl-octahydro-4,7-methano-inden-5-ol:
$^1$H NMR (CDCl$_3$, 400 MHz): 2.43-2.52 ppm (m, 1H), 1.95-2.05 ppm (m, 1H), 0.82-1.95 ppm (m, 8H), 1.35 ppm (s, 1H(OH)), 1.22 ppm (s, 3H), 0.99 ppm (d, 3H, J=6.20 Hz), 0.91 ppm (s, 3H), 0.55-0.80 ppm (m, 2H)

2,4,5-Trimethyl-octahydro-4,7-methano-inden-5-ol:
$^1$H NMR (CDCl$_3$, 400 MHz): 3.08 ppm (s, 1H(OH)), 2.05-2.14 ppm (m, 2H), 1.51-1.83 ppm (m, 6H), 1.23-1.35 ppm (m, 2H), 1.20 ppm (s, 3H), 1.08-1.12 ppm (m, 2H), 1.02 ppm (d, 3H, J=6.40 Hz), 1.00 ppm (s, 3H)

3(or 2),4,5-Trimethyl-octahydro-4,7-methano-inden-5-ol obtained as above was described as having strong patchouli, strong woody, strong earthy, and camphoraceous notes.

EXAMPLE IV

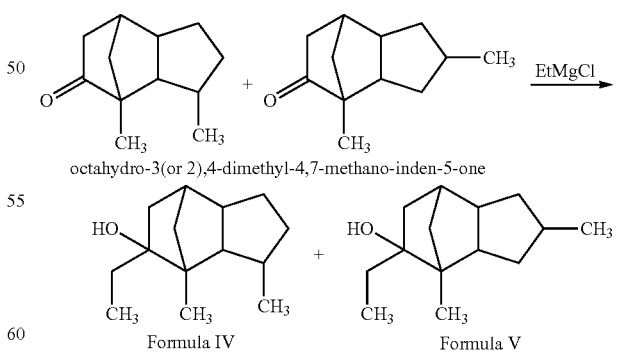
octahydro-3(or 2),4-dimethyl-4,7-methano-inden-5-one

Formula IV
Formula V

Preparation of 5-Ethyl-3(or 2),4-dimethyl-octahydro-4,7-methano-inden-5-ol (Formula IV and Formula V): A flame-dried, 3-L 3-neck reaction flask equipped with a mechanical stirrer, an addition funnel, a condenser, and a thermocouple was charged with ethyl magnesium chloride (EtMgCl) in THF (2 M, 0.8 L) under $N_2$. The temperature was cooled to and maintained at 15-20° C. using an external IPA cooling bath. Octahydro-3(or 2),4-dimethyl-4,7-methano-inden-5-one (250 g, 1.4 mol, prepared as above in Example II) was fed in the reaction flask over 3-4 hours. The reaction temperature was allowed to rise to and maintained at 30° C. for 1 hour. The reaction mixture was subsequently quenched with HOAc (90 g, 1.5 mol) and ice. The organic layer was washed once with dilute sodium carbonate solution (200 mL, 2%) and separated to afford the crude product, which was further distilled to afford 5-ethyl-3(or 2),4-dimethyl-octahydro-4,7-methano-inden-5-ol (a mixture of Formula IV and Formula V in a ratio of 60:40) with a boiling point of 131° C. at a pressure of 13 mmHg (156 g). Distillation was further employed to separate individual components.

5-Ethyl-3,4-dimethyl-octahydro-4,7-methano-inden-5-ol:

$^1$H NMR (CDCl$_3$, 400 MHz): 1.28-2.10 ppm (m, 10H), 0.88-1.13 ppm (m, 13H), 0.69-0.79 ppm (m, 1H)

5-ethyl-2,4-dimethyl-octahydro-4,7-methano-inden-5-ol:

$^1$H NMR (CDCl$_3$, 400 MHz): 2.51 ppm (q, 1H, J=8.32 Hz), 1.28-2.10 ppm (m, 9H), 0.88-1.13 ppm (m, 13H), 0.56-0.65 ppm (m, 1H)

5-Ethyl-3(or 2),4-dimethyl-octahydro-4,7-methano-inden-5-ol obtained as above was described as having weak earthy, piney, green, resinous, and camphoraceous notes.

EXAMPLE V

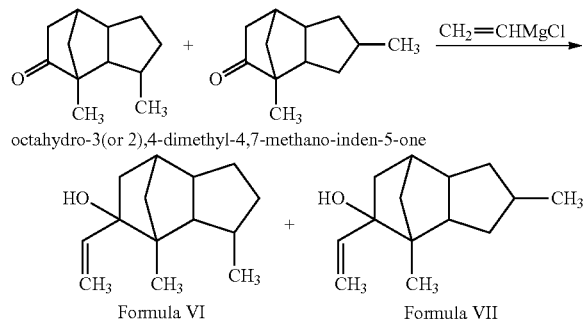

Preparation of 3(or 2),4-Dimethyl-5-vinyl-octahydro-4,7-methano-inden-5-ol (Formula VI and Formula VII): A flame-dried, 3-L 3-neck reaction flask equipped with a mechanical stirrer, an addition funnel, a condenser, and a thermocouple was charged with vinyl magnesium chloride (CH$_2$=CHMgCl) in THF (1.6 M, 2 L) under $N_2$. The temperature was cooled to and maintained at 15-20° C. using an external IPA cooling bath. Octahydro-3(or 2),4-dimethyl-4,7-methano-inden-5-one (475 g, 2.67 mol, prepared as above in Example II) was fed in the reaction flask over 3-4 hours. The reaction temperature was allowed to rise to and maintained at 30° C. for 1 hour. The reaction mixture was subsequently quenched with HOAc (180 g, 3.0 mol) and ice. The organic layer was washed once with dilute sodium carbonate solution (200 mL, 2%) and separated to afford the crude product, which was further distilled to afford 3(or 2),4-dimethyl-5-vinyl-octahydro-4,7-methano-inden-5-ol (a mixture of Formula VI and Formula VII in a ratio of 60:40) with a boiling point of 131° C. at a pressure of 13 mmHg (505 g). Distillation was further employed to separate individual components.

3,4-Dimethyl-5-vinyl-octahydro-4,7-methano-inden-5-ol:

$^1$H NMR (CDCl$_3$, 400 MHz): 6.01 ppm (d, 1H, J=17.21 Hz, ofd, J=10.80 Hz), 5.01-5.21 ppm (m, 2H), 1.06-2.17 (m, 11H), 1.00 ppm (d, 3H, J=6.08 Hz), 0.93-1.04 ppm (m, 1H), 0.84 ppm (s, 3H), 0.58-0.66 ppm (m, 1H)

2,4-Dimethyl-5-vinyl-octahydro-4,7-methano-inden-5-ol:

$^1$H NMR (CDCl$_3$, 400 MHz): 6.01 ppm (d, 1H, J=17.21 Hz, ofd, J=10.80 Hz), 5.01-5.21 ppm (m, 2H), 2.56 ppm (q, 1H, J=8.43 Hz), 1.06-2.17 ppm (m, 10H), 1.03 ppm (d, 3H, J=6.36 Hz), 0.93-1.04 ppm (m, 1H), 0.92 ppm (s, 3H), 0.68-0.78 ppm (m, 1H)

3(or 2),4-Dimethyl-5-vinyl-octahydro-4,7-methano-inden-5-ol obtained as above was described as having weak woody, weak earthy, green, and slightly camphoraceous notes.

EXAMPLE VI

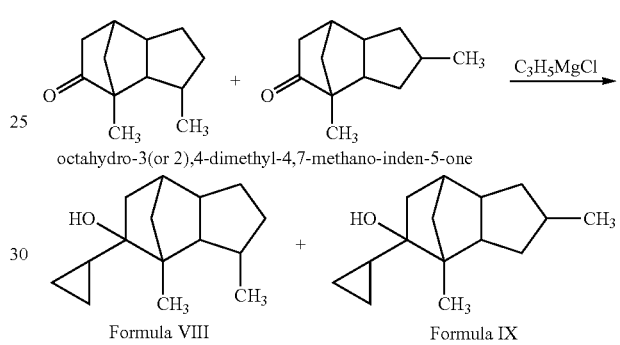

Preparation of 5-Cyclopropyl-3(or 2),4-dimethyl-octahydro-4,7-methano-inden-5-ol (Formula VIII and Formula IX): A flame-dried, 3-L 3-neck reaction flask equipped with a mechanical stirrer, an addition funnel, a condenser, and a thermocouple was charged with cyclopropyl magnesium chloride (C$_3$H$_5$MgCl) in THF (0.5 M, 1.55 L) under $N_2$. The temperature was cooled to and maintained at 15-20° C. using an external IPA cooling bath. Octahydro-3(or 2),4-dimethyl-4,7-methano-inden-5-one (126 g, 0.7 mol, prepared as above in Example II) was fed in the reaction flask over 3-4 hours. The reaction temperature was allowed to rise to and maintained at 30° C. for 1 hour. The reaction mixture was subsequently quenched with HOAc (60 g, 1.0 mol) and ice. The organic layer was washed once with dilute sodium carbonate solution (200 mL, 2%) and separated to afford the crude product, which was further distilled to afford 5-cyclopropyl-3(or 2),4-dimethyl-octahydro-4,7-methano-inden-5-ol (a mixture of Formula VIII and Formula IX in a ratio of 60:40) with a boiling point of 121° C. at a pressure of 2 mmHg (68 g). Distillation was further employed to separate individual components.

5-Cyclopropyl-3,4-dimethyl-octahydro-4,7-methano-inden-5-ol:

$^1$H NMR (CDCl$_3$, 400 MHz): 1.49-2.13 ppm (m, 7H), 0.84-1.40 ppm (m, 6H), 1.09 ppm (s, 3H), 0.93 ppm (s, 3H), 0.56-0.65 ppm (m, 1H), 0.25-0.43 ppm (m, 4H)

5-Cyclopropyl-2,4-dimethyl-octahydro-4,7-methano-inden-5-ol:

$^1$H NMR (CDCl$_3$, 400 MHz): 2.46 ppm (q, 1H, J=8.36 Hz), 1.49-2.13 ppm (m, 6H), 0.84-1.40 ppm (m, 6H), 1.03 ppm (s, 3H), 1.02 ppm (s, 3H), 0.70-0.80 ppm (m, 1H), 0.25-0.43 ppm (m, 4H)

5-Cyclopropyl-3(or 2),4-dimethyl-octahydro-4,7-methano-inden-5-ol obtained as above was described as having weak earthy, green, and fatty notes.

EXAMPLE VII

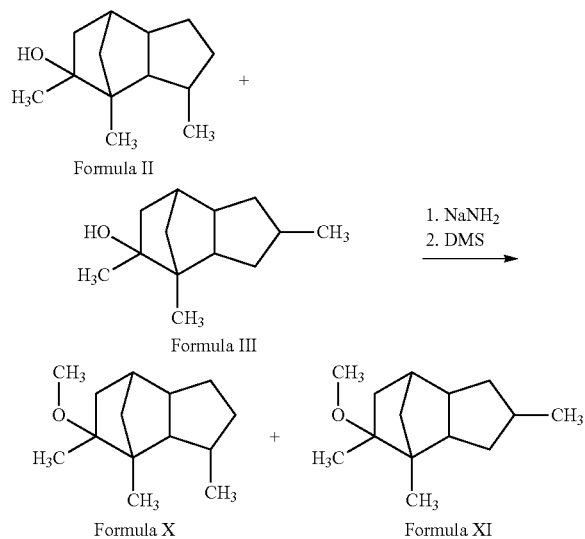

Preparation of 6-Methoxy-1,6,7-trimethyl-octahydro-4,7-methano-indene (Formula X) and 5-Methoxy-2,4,5-trimethyl-octahydro-4,7-methano-indene (Formula XI): A flame-dried, 3-L 3-neck reaction flask equipped with a mechanical stirrer, an addition funnel, a condenser, and a thermocouple was charged with toluene (800 g) and sodium amide (NaNH$_2$) (53 g, 1.36 mol). The temperature was heated to and maintained at about 100° C. 3(or 2),4,5-Trimethyl-octahydro-4,7-methano-inden-5-ol (a mixture of Formula II and Formula III in a ratio of 60:40, prepared as above in Example III) (240 g, 1.24 mol) was fed dropwise in the reaction flask over 2 hours. The reaction was monitored by the evolution of ammonium gas using litmus paper over the condenser. The reaction was aged for 2 hours after the feeding was complete and litmus paper no longer turned bright blue. The temperature was then cooled to 75° C. Dimethyl sulfate (DMS) (187 g, 1.48 mol) was fed dropwise in the reaction flask over 2 hours. The temperature was allowed to exothermic to 80-85° C. During the feeding of DMS, THF (200 g) was also added as a co-solvent. The reaction was aged for additional 3 hours and quenched with IPA (50 mL) followed by sodium hydroxide (NaOH) (960 g, 6.0 mol, 25%). The temperature was then heated to and maintained at about 80° C. for 2 hours. The obtained crude product was subsequently washed with water (1 L), HCl (500 mL, 2%), water (500 mL), and sodium carbonate solution (500 mL, 3%). Further distillation afforded methoxy-trimethyl-octahydro-4,7-methano-indenes (a mixture of Formula X and Formula XI in a ratio of 60:40) with a boiling point of 110° C. at a pressure of 10 mmHg (236 g). Distillation was further employed to separate individual components.

6-Methoxy-1,6,7-trimethyl-octahydro-4,7-methano-indene:
$^1$H NMR (CDCl$_3$, 400 MHz): 3.21 ppm (s, 3H), 1.18 ppm (s, 3H), 0.55-2.06 ppm (m, 18H)

5-Methoxy-2,4,5-trimethyl-octahydro-4,7-methano-indene:
$^1$H NMR (CDCl$_3$, 400 MHz): 3.21 ppm (s, 3H), 2.50-2.57 ppm (m, 1H), 1.18 ppm (s, 3H), 0.55-2.06 ppm (m, 17H)

The mixture of 6-methoxy-1,6,7-trimethyl-octahydro-4,7-methano-indene and 5-methoxy-2,4,5-trimethyl-octahydro-4,7-methano-indene obtained as above was described as having weak woody, piney, camphoraceous, and clay notes.

EXAMPLE VIII

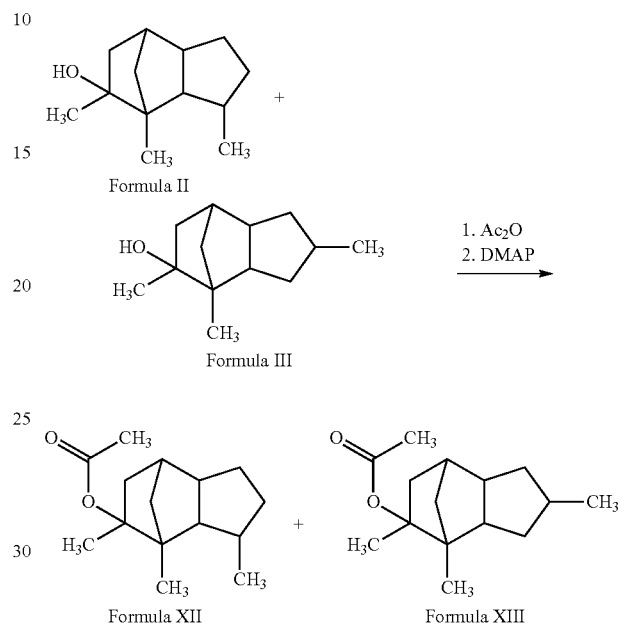

Preparation of Acetic acid 3(or 2),4,5-trimethyl-octahydro-4,7-methano-inden-5-yl ester (Formula XII and Formula XIII): A flame-dried, 2-L 3-neck reaction flask equipped with a mechanical stirrer, an addition funnel, a condenser, and a thermocouple was charged with 3(or 2),4,5-trimethyl-octahydro-4,7-methano-inden-5-ol (a mixture of Formula II and Formula III in a ratio of 60:40, prepared as above in Example III) (124 g, 0.64 mol), acetic anhydride (Ac$_2$O) (143 g, 1.4 mol), and 4-dimethylaminopyridine (DMAP) (2 g, 0.016 mol). The temperature was heated to and maintained at about 100° C. The reaction was aged for 6 hours. GC analysis indicated a conversion rate of about 70%. The obtained crude product was quenched with water and washed with dilute sodium carbonate solution. Distillation and further column chromatography afforded acetic acid 3(or 2),4,5-trimethyl-octahydro-4,7-methano-inden-5-yl ester (a mixture of Formula XII and Formula XIII in a ratio of 60:40) with a boiling point of 118° C. at a pressure of 6 mmHg (100 g). Distillation was further employed to separate individual components.

Acetic acid 3,4,5-trimethyl-octahydro-4,7-methano-inden-5-yl ester:
$^1$H NMR (CDCl$_3$, 400 MHz): 1.98 ppm (s, 3H), 1.48-1.97 ppm (m, 6H), 1.43 ppm (s, 3H), 1.09-1.40 ppm (m, 3H), 0.91-1.08 ppm (m, 8H), 0.58-0.79 ppm (m, 1H)

Acetic acid 2,4,5-trimethyl-octahydro-4,7-methano-inden-5-yl ester:
$^1$H NMR (CDCl$_3$, 400 MHz): 2.47 ppm (q, 1H, J=8.42 Hz), 1.97 ppm (s, 3H), 1.48-1.97 ppm (m, 5H), 1.43 ppm (s, 3H), 1.09-1.40 ppm (m, 3H), 0.91-1.08 ppm (m, 8H), 0.58-0.79 ppm (m, 1H)

Acetic acid 3(or 2),4,5-trimethyl-octahydro-4,7-methano-inden-5-yl ester obtained as above was described as having weak woody, creamy, amber sweet, and cedar notes.

EXAMPLE IX

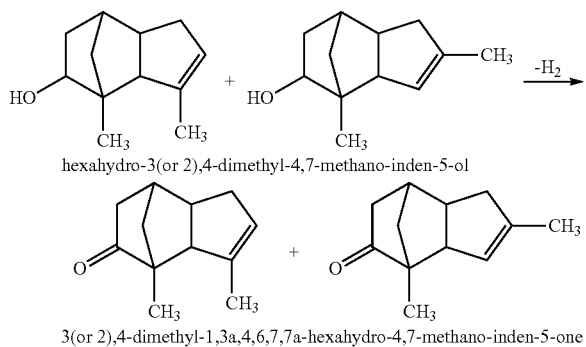

hexahydro-3(or 2),4-dimethyl-4,7-methano-inden-5-ol

3(or 2),4-dimethyl-1,3a,4,6,7,7a-hexahydro-4,7-methano-inden-5-one

Preparation of 3(or 2),4-Dimethyl-1,3a,4,6,7,7a-hexahydro-4,7-methano-inden-5-one: A 5-L 3-neck reaction flask equipped with a mechanical stirrer, an addition funnel, a Dean-Stark trap, a condenser, a nitrogen ($N_2$) bubbler, and a thermocouple was charged with hexahydro-3(or 2),4-dimethyl-4,7-methano-inden-5-ol (a mixture of hexahydro-3,4-dimethyl-4,7-methano-inden-5-ol and hexahydro-2,4-dimethyl-4,7-methano-inden-5-ol in a ratio of 60:40) (150 g, 0.84 mol, commercially available at IFF), Primol (50 g), and Pri-Cat CZ 30/18 P (64 g). The reaction temperature was heated to 240° C. Hydrogen gas ($H_2$) evolution was monitored via the N2 bubbler. Once the $H_2$ was observed, additional octahydro-3(or 2),4-dimethyl-4,7-methano-inden-5-ol (1.46 Kg, 8.19 mol) was fed in the reaction flask over 4 hours. After the feeding was complete, the reaction was aged for additional 2 hours. Gas-liquid chromatogrpahy (GLC) indicated a conversion rate of ~95%. The crude product was filtered and distilled to afford 3(or 2),4-dimethyl-1,3a,4,6,7,7a-hexahydro-4,7-methano-inden-5-one (a mixture of 3,4-dimethyl-1,3a,4,6,7,7a-hexahydro-4,7-methano-inden-5-one and 2,4-dimethyl-1,3a,4,6,7,7a-hexahydro-4,7-methano-inden-5-one in a ratio of 60:40) with a boiling point of 104° C. at a pressure of 7.0 mmHg (1.445 Kg).

EXAMPLE X

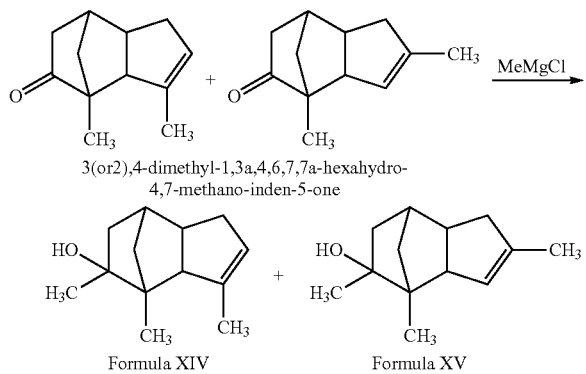

3(or2),4-dimethyl-1,3a,4,6,7,7a-hexahydro-4,7-methano-inden-5-one

Formula XIV   Formula XV

Preparation of 3(or 2),4,5-Trimethyl-3a,4,5,6,7,7a-hexahydro-4,7-methano-inden-5-ol (Formula XIV and Formula XV): A flame-dried, 5-L 3-neck reaction flask equipped with a mechanical stirrer, an addition funnel, a condenser, and a thermocouple was charged with MeMgCl in THF (3 M, 1.6 L) under $N_2$. The temperature was cooled to and maintained at 15-20° C. using an external isopropyl alcohol (IPA) cooling bath. 3(or 2),4-Dimethyl-1,3a,4,6,7,7a-hexahydro-4,7-methano-inden-5-one (405 g, 2.3 mol, prepared as above in Example IX) was fed in the reaction flask over 3-4 hours. The reaction temperature was allowed to rise to 25-30° C. and maintained at 30° C. for 1 hour. The reaction mixture was subsequently quenched with acetic acid (HOAc) (180 g, 3.0 mol) and ice. The organic layer was washed once with dilute sodium carbonate solution (500 mL, 2%) and separated to afford a crude product, which was then distilled to afford 3(or 2),4,5-trimethyl-3a,4,5,6,7,7a-hexahydro-4,7-methano-inden-5-ol (a mixture of Formula XIV and Formula XV in a ratio of 60:40) with a boiling point of 99° C. at a pressure of 2.5 mmHg (318 g). Distillation was further employed to separate individual components.

3,4,5-Trimethyl-3a,4,5,6,7,7a-hexahydro-4,7-methano-inden-5-ol:

$^1$H NMR (CDCl$_3$, 500 MHz): 5.39 ppm (br, 1H), 3.00 ppm (br, 1H), 2.20-2.28 ppm (m, 2H), 1.60-1.88 ppm (m, 3H), 1.76 ppm (s, 3H), 1.22 ppm (s, 3H), 1.07-1.37 ppm (m, 4H), 1.03 ppm (s, 3H)

3 (or 2),4,5-Trimethyl-3a,4,5,6,7,7a-hexahydro-4,7-methano-inden-5-ol:

$^1$H NMR (CDCl$_3$, 500 MHz): 5.15 ppm (br, 1H), 3.15 ppm (br, 1H), 2.20-2.28 ppm (m, 2H), 1.60-1.88 ppm (m, 3H), 1.70 ppm (s, 3H), 1.21 ppm (s, 3H), 1.07-1.37 ppm (m, 4H), 0.93 ppm (s, 3H)

3(or 2),4,5-Trimethyl-3a,4,5,6,7,7a-hexahydro-4,7-methano-inden-5-ol obtained as above was described as having weak woody, weak earthy, and camphoraceous notes.

EXAMPLE XI

The fragrance properties of the compounds obtained in the above examples were evaluated using an intensity scale of 0 to 3, where 0=none, 1=weak, 2=moderate, 3=strong. Averaged sensory scores were reported in the following:

| No. | Compound | Odor Profile | Odor Intensity |
|---|---|---|---|
| 1 | Octahydro-3(or 2),4-dimethyl-4,7-methano-inden-5-ol (EXAMPLE I) | weak woody, weak patchouli, and camphoraceous | 1 |
| 2 | Octahydro-3(or 2),4-dimethyl-4,7-methano-inden-5-one (EXAMPLE II) | weak woody, weak earthy, and camphoraceous | 1 |
| 3 | Formula II/Formula III (EXAMPLE III) | strong patchouli, strong woody, strong earthy, and camphoraceous | 3 |
| 4 | Formula IV/Formula V (EXAMPLE IV) | weak earthy, piney, green, resinous, and camphoraceous | 1 |
| 5 | Formula VI/Formula VII (EXAMPLE V) | weak woody, weak earthy, green, and slightly camphoraceous | 1 |
| 6 | Formula VIII/Formula IX (EXAMPLE VI) | weak earthy, green, and fatty | 1 |
| 7 | Formula X/Formula XI (EXAMPLE VII) | weak woody, piney, and clay | 1 |

-continued

| No. | Compound | Odor Profile | Odor Intensity |
|---|---|---|---|
| 8 | Formula XII/Formula XIII (EXAMPLE VIII) | weak woody, creamy, amber sweet, and cedar | 1 |
| 9 | Formula XIV/Formula XV (EXAMPLE X) | weak woody, weak earthy, and camphoraceous | 1 |

Compound No. 3 (Formula II/Formula III obtained in EXAMPLE III) exhibited unexpected strong and long-lasting patchouli, woody, earthy, and camphoraceous characters, superior to all other structurally closely related analogs.

EXAMPLE XII

Preparation and Evaluation of 3(or 2),4,5-Trimethyl-octahydro-4,7-methano-inden-5-ol Mixture of Different Ratios: 3(or 2),4,5-Trimethyl-octahydro-4,7-methano-inden-5-ol mixture (prepared as above in EXAMPLE III) was further carefully distilled through a GOODLOE column with high theoretical plates to afford a series of mixtures of different mixing ratios.

The following specific mixture samples were evaluated for odor properties:

| No. | Formula II (% by weight) | Formula III (% by weight) | Odor Profile |
|---|---|---|---|
| 1 | 65 | 35 | Strong patchouli, strong woody, strong earthy, and camphoraceous. Acceptable. |
| 2 | 60 | 40 | Strong patchouli, strong woody, strong earthy, and camphoraceous. Acceptable. |
| 3 | 55 | 45 | Strong patchouli, strong woody, strong earthy, and camphoraceous. Acceptable. |
| 4 | 51 | 49 | Strong patchouli, strong woody, strong earthy, and camphoraceous. Acceptable. |
| 5 | 40 | 60 | Patchouli with additional piney and resinous. Undesirable. |
| 6 | 35 | 65 | Patchouli with additional piney and resinous. Undesirable. |

The above evaluation demonstrated that samples 1-4 were superior to samples 5 and 6. Specifically, only a 3(or 2),4,5-trimethyl-octahydro-4,7-methano-inden-5-ol mixture containing no less than 50% by weight of 3,4,5-trimethyl-octahydro-4,7-methano-inden-5-ol was found to possess desirable fragrance properties of high strength.

What is claimed is:
1. A compound of formula:

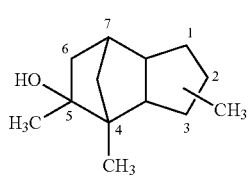

Formula I wherein a methyl group is bonded to the 5-membered ring at position 2 or 3, or a mixture thereof.
2. The compound of claim 1, wherein the compound is selected from the group consisting of 3,4,5-trimethyl-octahydro-4,7-methano-inden-5-ol; 2,4,5-trimethyl-octahydro-4,7-methano-inden-5-ol; and a mixture of 3,4,5-trimethyl-octahydro-4,7-methano-inden-5-ol and 2,4,5-trimethyl-octahydro-4,7-methano-inden-5-ol.

3. A method of improving, enhancing or modifying a fragrance formulation through the addition of an olfactory acceptable amount of a compound of formula:

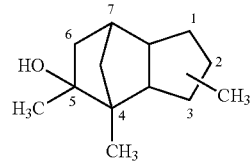

Formula I wherein a methyl group is bonded to the 5-membered ring at position 2 or 3, or a mixture thereof.
4. The method of claim 3, wherein the compound is selected from the group consisting of 3,4,5-trimethyl-octahydro-4,7-methano-inden-5-ol; 2,4,5-trimethyl-octahydro-4,7-methano-inden-5-ol; and a mixture of 3,4,5-trimethyl-octahydro-4,7-methano-inden-5-ol and 2,4,5-trimethyl-octahydro-4,7-methano-inden-5-ol.
5. The method of claim 4, wherein the compound is a mixture of 3,4,5-trimethyl-octahydro-4,7-methano-inden-5-ol and 2,4,5-trimethyl-octahydro-4,7-methano-inden-5-ol, and wherein the mixture contains no less than 50% by weight of 3,4,5-trimethyl-octahydro-4,7-methano-inden-5-ol.
6. The method of claim 3, wherein the fragrance formulation is incorporated into a product selected from the group consisting of a perfume, a cologne, a toilet water, a cosmetic product, a personal care product, a fabric care product, a cleaning product, and an air freshener.
7. The method of claim 6, wherein the cleaning product is selected from the group consisting of a detergent, a dishwashing composition, a scrubbing compound, and a window cleaner.
8. The method of claim 3, wherein the olfactory acceptable amount is from about 0.005 to about 50 weight percent of the fragrance formulation.
9. The method of claim 3, wherein the olfactory acceptable amount is from about 0.5 to about 25 weight percent of the fragrance formulation.
10. The method of claim 3, wherein the olfactory acceptable amount is from about 1 to about 10 weight percent of the fragrance formulation.
11. A fragrance formulation containing an olfactory acceptable amount of a compound of formula:

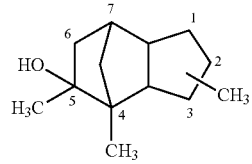

Formula I wherein a methyl group is bonded to the 5-membered ring at position 2 or 3, or a mixture thereof.
12. The fragrance formulation of claim 11, wherein the compound is selected from the group consisting of 3,4,5-trimethyl-octahydro-4,7-methano-inden-5-ol; 2,4,5-trimethyl-octahydro-4,7-methano-inden-5-ol; and a mixture of 3,4,5-trimethyl-octahydro-4,7-methano-inden-5-ol and 2,4,5-trimethyl-octahydro-4,7-methano-inden-5-ol.

13. The fragrance formulation of claim 12, wherein the compound is a mixture of 3,4,5-trimethyl-octahydro-4,7-methano-inden-5-ol and 2,4,5-trimethyl-octahydro-4,7-methano-inden-5-ol, and wherein the mixture contains no less than 50% by weight of 3,4,5-trimethyl-octahydro-4,7-methano-inden-5-ol.

14. The fragrance formulation of claim 11 incorporated into a product selected from the group consisting of a perfume, a cologne, toilet water, a cosmetic product, a personal care product, a fabric care product, a cleaning product, and an air freshener.

15. The fragrance formulation of claim 14, wherein the cleaning product is selected from the group consisting of a detergent, a dishwashing composition, a scrubbing compound, and a window cleaner.

16. The fragrance formulation of claim 11, wherein the mixture is incorporated at a level of from about 0.005 to about 50 weight percent of the product.

17. The fragrance formulation of claim 11, wherein the mixture is incorporated at a level of from about 0.5 to about 25 weight percent of the product.

18. The fragrance formulation of claim 11, wherein the mixture is incorporated at a level of from about 1 to about 10 weight percent of the product.

19. A fragrance product containing an olfactory acceptable amount of the compound of claim 1.

20. The fragrance product of claim 19, wherein the compound is a mixture of 3,4,5-trimethyl-octahydro-4,7-methano-inden-5-ol and 2,4,5-trimethyl-octahydro-4,7-methano-inden-5-ol, and wherein the mixture contains no less than 50% by weight of 3,4,5-trimethyl-octahydro-4,7-methano-inden-5-ol.

* * * * *